United States Patent
Yew (10) Patent No.: US 6,667,174 B2
(45) Date of Patent: Dec. 23, 2003

(54) EXPRESSION VECTORS CONTAINING HYBRID UBIQUITIN PROMOTERS

(75) Inventor: Nelson Yew, West Upton, MA (US)

(73) Assignee: Genzyme Corporation, Cambridge, MA (US)

( * ) Notice: Subject to any disclaimer, the term of this patent is extended or adjusted under 35 U.S.C. 154(b) by 51 days.

(21) Appl. No.: 09/952,152

(22) Filed: Sep. 13, 2001

(65) Prior Publication Data

US 2002/0090719 A1 Jul. 11, 2002

Related U.S. Application Data

(60) Provisional application No. 60/233,938, filed on Sep. 18, 2000, and provisional application No. 60/259,567, filed on Jan. 3, 2001.

(51) Int. Cl.[7] ............................................... C12N 15/85
(52) U.S. Cl. ................... 435/320.1; 435/69.1; 536/24.1
(58) Field of Search ............................ 435/320.1, 69.1; 536/24.1

(56) References Cited

PUBLICATIONS

Schorpp et al., Nucleic Acids Research, vol. 24, No. 9, 1996, pp. 1787–1788.*
Moser et al., Biotechnol. Prog., vol. 16, Sep. 8, 2000, pp. 724–735.*
Ciechanover, A et al., Ubiquitin–mediated proteolysis: biological regulation via destruction, Bioessays, vol. 22, 2000, pp. 442–451.
Spencer, V. A. et al., Role of covalent modifications of histones in regulating gene expression, Gene, vol. 240, 1999, PP 1–12.
Li, S. et al., Effect of immune response on gene transfer to the lung via systemic administration of cationic lipidic vectors, Am. J. Physiol., vol. 276, 1999, pp. L796–804.
Tousignant, J. et al., Comprehensive Analysis of the Acute Toxicities Induced by Systemic Administration of Cationic Lipid:Plasmid DNA Complexes in Mice, Hum. Gene Ther., vol. 11, 2000, PP2493–2513.
Boshart, M. et al., A Very Strong Enhancer Is Located Upstream of an Immediate Early Gene of Human Cytomegalovirus, Cell, vol. 41, 1985, pp. 521–530.
Zweidler–McKay, P.A. et al., Gfi Encodes a Nuclear Zinc Finger Protein That Binds DNA and Functions as a Transcriptional Repressor, Mol. Cell. Biol. vol. 16, No. 8, pp. 4024–4034.
Galvin, K. et al., Multiple Mechanisms of Transcriptional Repression by YY1, Mol. cell. Bio., vol. 17, No. 7, 1997, pp. 3723–3732.
Lee, E. R. et al., Detailed Analysis of Structures and Formulations of Cationic Lipids for Efficient Gene Transfer to the Lung, Hum. Gene Ther., vol. 7, 1996, pp. 1701–1717.
Baker, R. T. et al., The human ubiquitin gene family: structure of a gene and pseudogenes from the Ub B subfamily, Nucleic Acids Res., vol. 15, No. 2, 1987, PP443–463.
Yew, N. S. et al ., Optimization of Plasmid Vectors for High – Level Expression in Lung Epithelial Cells, Hum. Gene Ther., vol. 8, 1997, pp. 575–584.

\* cited by examiner

*Primary Examiner*—James Ketter (57) ABSTRACT

Sustained transgene expression will be required for the vast majority of genetic diseases being considered for gene therapy. The initially high levels of expression attained with plasmid DNA (pDNA) vectors containing viral promoters, such as that from cytomegalovirus (CMV), decline precipitously to near background levels within 2 to 3 weeks. We have constructed pDNA vectors containing the human cellular ubiquitin B (Ub) promoter and evaluated their expression in the mouse lung. Cationic lipid-pDNA complexes were instilled intranasally (IN) or injected intravenously (IV) into immunodeficient BALB/c mice. Chloramphenicol acetyltransferase (CAT) reporter gene expression from the Ub promoter was initially very low at day 2 post-administration but by day 35 exceeded the level of expression attained from a CMV promoter vector by 4- to 9-fold. Appending a portion of the CMV enhancer 5' of the Ub promoter (CMV-Ub) increased CAT expression to nearly that of the CMV promoter and expression persisted in the lung for at least three months, with 50% of day 2 levels remaining at day 84. In the liver, expression from the CMV-Ub hybrid promoter was sustained for 42 days. Since previous studies have shown that eliminating immunostimulatory CpG motifs in pDNA vectors reduces their toxicity, we constructed a CpG deficient version of the CMV-Ub vector expressing alpha-galactosidase A, the enzyme that is deficient in Fabry disease, a lysosomal storage disorder. After IN or IV administration, levels of alpha-galactosidase A from this vector were not only undiminished but increased 500% to 1500% by day 35. These results suggest that CpG-reduced plasmid vectors containing a CMV-Ub hybrid promoter may provide the long-term expression and efficacy required for a practical gene therapeutic.

11 Claims, 8 Drawing Sheets

EXPRESSION VECTORS CONTAINING HYBRID UBIQUITIN PROMOTERS

This Appln claims benefit of prov. No. 60/233,938 filed Sep. 18, 2000 and No. 60/259,567 filed Jan. 3, 2001.

FIELD OF THE INVENTION

The present invention relates to expression vectors that contain hybrid ubiquitin promoters. The promoters are useful, among other uses, for high and sustained transgene expression in in vivo and ex vivo gene therapy and for recombinant protein expression in vitro.

BACKGROUND OF THE INVENTION

Ubiquitin is an abundant, small, 76 amino acid protein that is expressed in all eukaryotic cells (Ciechanover et al. 2000; Wilkinson et al, 2000). The protein covalently attaches to abnormal, misfolded or short-lived proteins, marking them for destruction in proteasomes (Ciechanover, supra). Ubiquitin also associates with histones and may play a role in the regulation of gene expression (Spencer and Davie, 1999). The coding sequence is remarkably conserved evolutionarily, being identical from insect to man. There are at least three known ubiquitin genes in humans, named UbA, UbB, and UbC, which appear to contain one, three or nine precise direct repeats of the 76 amino acid coding unit, respectively (Baker and Board, *Nucleic Acids Research*, 15:443–463 (1987); Lund et al. 1985; Nenoi, et al 1996; and Wiborg et al., *EMBO J.*, 4:755–759 (1985). The human UbB and UbC genes have been sequenced and shown to contain no introns within their coding regions, but each contain an intron in the 5' flanking region (Baker and Board, supra; Nenoi supra). The UbC promoter has been shown to provide high level, ubiquitous expression when inserted into transgenic mice and when incorporated into plasmid DNA vectors (Johansen et al., *FEBS* 267:289–294 (1990); Schorpp et al., *Nucleic Acids Research*, 24:1787–1788 (1996); Wulff et al., 1990).

The promoter from human cytomegalovirus (CMV) (see U.S. Pat. Nos. 5,849,522; 5,168,062) is known to provide strong constitutive expression of transgenes at high levels. However, in gene therapy applications, expression levels achieved using the CMV promoter have been shown to be significantly reduced over time.

Accordingly, there remains a need to provide improved regulatory elements that are able to provide high and sustained expression of transgenes in applications such as gene therapy.

SUMMARY OF THE INVENTION

The present invention provides hybrid regulatory regions using elements from one or more ubiquitin promoters together with one or more strong enhancers. The present invention further provides DNA vectors that provide for high and persistent expression of associated coding sequences.

BRIEF DESCRIPTION OF THE DRAWINGS

FIG. 1. Diagram of plasmid DNA vectors. Ub, human ubiquitin B promoter; Intron, a hybrid of an adenoviral and mouse immunoglobulin gene intron; SEAP, secreted human placental alkaline phosphatase cDNA; pA, bovine growth hormone polyadenylation signal; Ub intron, the endogenous intron in the UBB gene; CAT, chloramphenicol acetyltransferase cDNA; CMV enh, human cytomegalovirus immediate early gene enhancer region (−522 to −219 relative to the transcription start site); CMV, cytomegalovirus immediate early gene enhancer-promoter (−522 to +78 relative to the start site).

FIG. 3. Persistence of CAT expression from pUBI-CAT in the mouse lung. A) 75 µl of cationic lipid GL-67 complexed with either pUBI-CAT or pCF1-CAT (0.6:3.6 mM GL-67:pDNA) was instilled intranasally into nude BALB/c mice. Lungs were harvested at different days post-injection and the levels of CAT in the lung homogenates were measured. B) 100 µl of cationic lipid GL-62 complexed with either pUBI-CAT or pCF1-CAT (0.75:0.75 mM GL-62:pDNA) was injected via the tail vein into nude BALB/c mice. Lungs were harvested at different days post-injection and the levels of CAT in the lung homogenates were measured. n=4 mice per timepoint. Data are expressed as mean±SEM.

FIG. 4. Persistence of CAT expression from pCUBI-CAT in the mouse lung. A) 75 µl of cationic lipid GL-67 complexed with either pCUBI-CAT or pCF1-CAT (0.6:3.6 mM GL-62:pDNA) was instilled intranasally into nude BALB/c mice. Lungs were harvested at different days post-injection and the levels of CAT in the lung homogenates were measured. B) Groups of mice were instilled with a second dose of GL-67:pCUBI-CAT complex at day 26. Lungs were harvested at days 28 and 84 (after the first dose) and CAT assays were performed. n=4 mice per group. Data are expressed as mean±SEM.

FIG. 6. Diagram of α-galactosidase A vectors. CMV enh, human cytomegalovirus immediate early gene enhancer region (−522 to −219 relative to the transcription start site), Ub, human ubiquitin B promoter; Ub intron, the endogenous intron in the UBB gene; HAGA, human α-galactosidase cDNA; BGH pA, bovine growth hormone polyadenylation signal; ori-min, minimal origin of replication region; Kan-syn, synthetic, non-CpG kanamycin resistance gene. pGZA-HAGA is identical except the entire CMV promoter is in place of the CMV-Ub promoter.

FIG. 8. Sequence of the CMV enhancer-ubiquitin B promoter and intron region. The CMV enhancer region extends from −522 to −219 relative to the transcriptional start site. Binding sites for the transcription factors Sp1, CREB/ATF, and NF B are indicated. The UbB promoter region begins at −1093 relative to the translational ATG start site. The putative TATA box is outlined and the possible cap site is indicated by the filled triangle. The intron region is in lower case letters. Two direct repeats within the UbB intron are indicated by an overhead line.

DETAILED DESCRIPTION OF THE INVENTION

DNA vectors in which the ubiquitin B promoter drives the chloramphenicol acetyltransferase (CAT) reporter gene resulted in persistent expression, albeit at low levels. A hybrid was constructed in which the CMV enhancer and ubiquitin B promoter were ligated together to express CAT. The result was persistent expression at significantly higher levels than the ubiquitin B promoter alone. Persistent expression using the hybrid ubiquitin promoters of the present invention has been achieved in various tissues, including lung and liver.

In preferred embodiments, an expression vector is constructed in which the promoter is isolated from the human ubiquitin A, ubiquitin B or ubiquitin C genes, or from ubiquitin genes of other species. The preferred enhancers include the human and murine cytomegalovirus (CMV) enhancers (see U.S. Pat. Nos. 5,849,522; 5,168,062), elongation factor 1-alpha enhancer, endothelial-specific enhancers and liver-specific enhancers, as well as other constitutive or inducible enhancer elements which are able to support expression, particularly in the lung.

In other preferred embodiments, plasmid vectors may be fully or partially deleted for immunostimulatory CpG sequences. Methods and materials for preparing such CpG-deleted plasmids and DNA sequences are disclosed in PCT publication WO 00/14262, the disclosure of which is hereby incorporated by reference.

Among the preferred therapeutic genes for delivery to cells are the hematopoietic factors, including Factor VIIa [U.S. Pat. No. 4,784,950]; Factor VIII [U.S. Pat. Nos. 4,965,199; 4,868,112 [B-domain deleted] and U.S. Pat. No. 5,661,008]; and Factor IX [U.S. Pat. No. 4,994,371]. Other preferred transgenes are those which encode lysosomal storage enzymes, including genes encoding glucocerebrosidase [Gaucher disease; U.S. Pat. Nos. 5,879,680; 5,236, 838]; alpha-galactosidase [Fabry disease; U.S. Pat. No. 5,401,650]; acid alpha-glucosidase [Pompe disease; WO00/ 12740]; alpha-nacetylgalactosaminidase [Schindler disease; U.S. Pat. No. 5,382,524]; acid sphingomyelinase [Niemann-Pick disease; U.S. Pat. No. 5,686,240]; alpha-iduronidase [WO9310244A1]. Other preferred transgenes include the genes for the cystic fibrosis transmembrane conductance regulator (CFTR), dystrophin, insulin and alpha-1-antitrypsin. The disclosures of all of the above publications are hereby incorporated herein by reference.

Sustained gene expression will be required for many genetic diseases being considered for gene therapy as well as for recombinant protein expression in vitro. Expression is often transient from plasmid DNA (pDNA) vectors containing viral promoters, such as that from cytomegalovirus (CMV). We have constructed expression vectors containing the chloramphenicol acetyltransferase (CAT) reporter gene expressed from the ubiquitin B promoter (pUBI-CAT) and evaluated their persistence of expression in the mouse lung. Cationic lipid-pDNA complexes were administered intranasally into nude BALB/c mice and levels of CAT in the lung were assayed. CAT expression from pUBI-CAT was initially low but then increased to levels 4–9 fold higher than from a vector employing the CMV promoter (pCF1-CAT) at day 35. We then appended the CMV enhancer to the 5' end of the UbB promoter. CAT expression from this vector (pCUBI-CAT) was equivalent to pCF1-CAT at day 2 and was 40-fold higher than from pCF1-CAT at day 58. Since previous studies have shown that eliminating immunostimulatory CpG motifs in pDNA vectors reduces their toxicity, we have also constructed CpG deficient versions of pCUBI-CAT, and we have synthesized CpG deficient, codon-optimized cDNAs encoding alpha-galactosidase, glucocerebrosidase, and Factor IX for insertion into the pCUBI vector. This combination of a persistent promoter and CpG reduction may provide the greater persistence and efficacy required for commercially viable gene therapeutic.

Durable, therapeutic levels of a gene product from a given dose of a gene therapy vector are desired for many disease indications. We have shown here that transgene expression from pDNA vectors containing the human ubiquitin B promoter can be highly stable, and has the unique property of actually increasing over time in some situations. When the strong enhancer elements of the human CMV promoter were appended to the Ub promoter, reporter gene expression from the CMV-Ub hybrid promoter was robust and persisted for at least three months in the lung. Expression of a therapeutic transgene, alpha-galactosidase A, was also sustained with levels increasing steadily during the one month period of the study.

The finding that long-term transgene expression could be maintained from an episomal pDNA supports the contention that the major limiting factor for sustained expression is promoter activity. Systems that increase the stability of pDNA in the cell, such as the use of nuclear retention elements, replication origins, or eukaryotic transposons, do aid in prolonging gene expression [1,2,27]. But after the initial massive loss of input pDNA, extremely low but detectable levels of pDNA have been shown to be stably maintained in the tissues for several months [3,28]. The target cells for most synthetic vectors, either the lung epithelial or endothelial cells (for cationic lipid-pDNA complexes), the liver hepatocytes, or skeletal muscle, are fully differentiated and have a very low turnover [29]. Our results indicate that the residual amounts of pDNA present in the transduced tissue are sufficiently stable to confer sustained expression.

The mechanism for the sustained transcriptional activity from the ubiquitin promoter is not known, and we can only speculate that the activity may at least partly relate to the normal functions of ubiquitin in the cell. Ubiquitin is required constitutively for removing abnormal or misfolded proteins, as well as the modification of histones leading to gene activation, and so may not be subject to the downregulation observed with many viral promoters [12,14]. Ubiquitin is also induced in response to cell stress, and expression may possibly be upregulated in response to the cellular necrosis and apoptosis known to be associated with administration of cationic lipid-pDNA complexes, which may explain the observed increase in expression over time [25, 30]. Other possibilities are that the promoter may be repressed at early timepoints, or that there is a gradual recruitment of transcription factors to the promoter over time.

A search for potential transcription factor binding sites in the Ub promoter found possible sites for CEBP/B, CREB, GATA-2, Sp1, and others, but the actual factors associated with this promoter will require further analysis. The CMV enhancer region used in the CMV-Ub hybrid adds multiple Sp1, CREB, and NFKB sites, contributing to the significantly increased transcriptional activity [31]. However, unlike CMV, the CMV-Ub hybrid was not downregulated over time. The CMV enhancer sequence used in CMB-Ub avoids some known repressor binding sites, such as the sites for the cellular Gfi repressor, but still contains sites for YY1, which can function as a repressor [32,33]. The CMV sequence alone without the Ub promoter also did not confer persistent expression by itself (data not shown). Somehow the array of factors involved with the Ub portion of the hybrid promoter appears to have overridden the normal inactivation of CMV and maintained activity.

The results shown here using the alpha-galactosidase A vectors suggest that eliminating CpG motifs within the plasmid also affected the inactivation of CMV over time. The pGZA-HAGA vector, containing an unmodified CMV promoter but a CpG reduced backbone, was significantly more persistent after IN delivery than its non-CpG reduced counterpart (FIG. 7A). The vector was not as persistent after IV delivery, but the decrease in expression was much less than is usually observed with a non-CpG reduced vector. Although the mechanism underlying this effect is unclear, immunostimulatory CpG motifs have been shown to play a major role in the inflammatory response associated with cationic lipid-pDNA complexes and to consequently inhibit transgene expression from pDNA vectors [34,35]. The loss of expression could occur by direct inhibition of promoter activity or by elimination of transfected cells due to a CTL response to the immunostimulatory CpG motifs [36]. Thus, reducing this negative effect by decreasing the content of immunostimulatory CpG motifs and incorporating the inherently more persistent CMV-Ub promoter, one could anticipate an expression profile that is a composite of both positive factors, and the data appear to support this conjecture.

Despite the improved performance of these vectors, the levels of alpha-galactosidase A that could be attained after IV or IN delivery were still below what would be required to be therapeutic [23]. One ongoing approach to this problem is to develop gene transfer vehicles that are more potent than current cationic lipid-pDNA formulations. However, given the sustained and steadily increasing levels of alpha-galactosidase A observed (FIG. 7), it may also be feasible to increase overall levels by multiple redosing of the vector. One would predict that repeat dosing would result in significantly higher levels of expression than could be achieved with a single dose. This possibility is currently being investigated.

The CMV-ubiquitin hybrid promoter will be useful in any in vitro or in vivo application requiring sustained gene expression. In the context of gene therapy, this may include pulmonary diseases, such as cystic fibrosis and alpha-1-antitrypsin deficiency, as well as other inherited genetic disorders such as hemophilia, urea cycle disorders, familial hypercholesterolemia, phenylketonuria, and the family of lysosomal storage disorders. For certain diseases the lung or liver can potentially serve as a depot organ for secretion of the protein into the bloodstream. This will necessarily require fairly sustained expression to achieve sufficient therapeutic levels in the blood for the protein to in turn be taken up by the target organs. The CMV-ubiquitin hybrid promoter may also be useful in the context of viral vectors (e.g. adenovirus and adeno-associated virus vectors) and in other tissues such as muscle or brain. There are still significant limitations to be addressed with synthetic gene delivery vectors, but the ability to confer sustained gene expression from the CMV-ubiquitin hybrid promoter will provide an important component of a practical and effective gene therapeutic.

Figure 1:
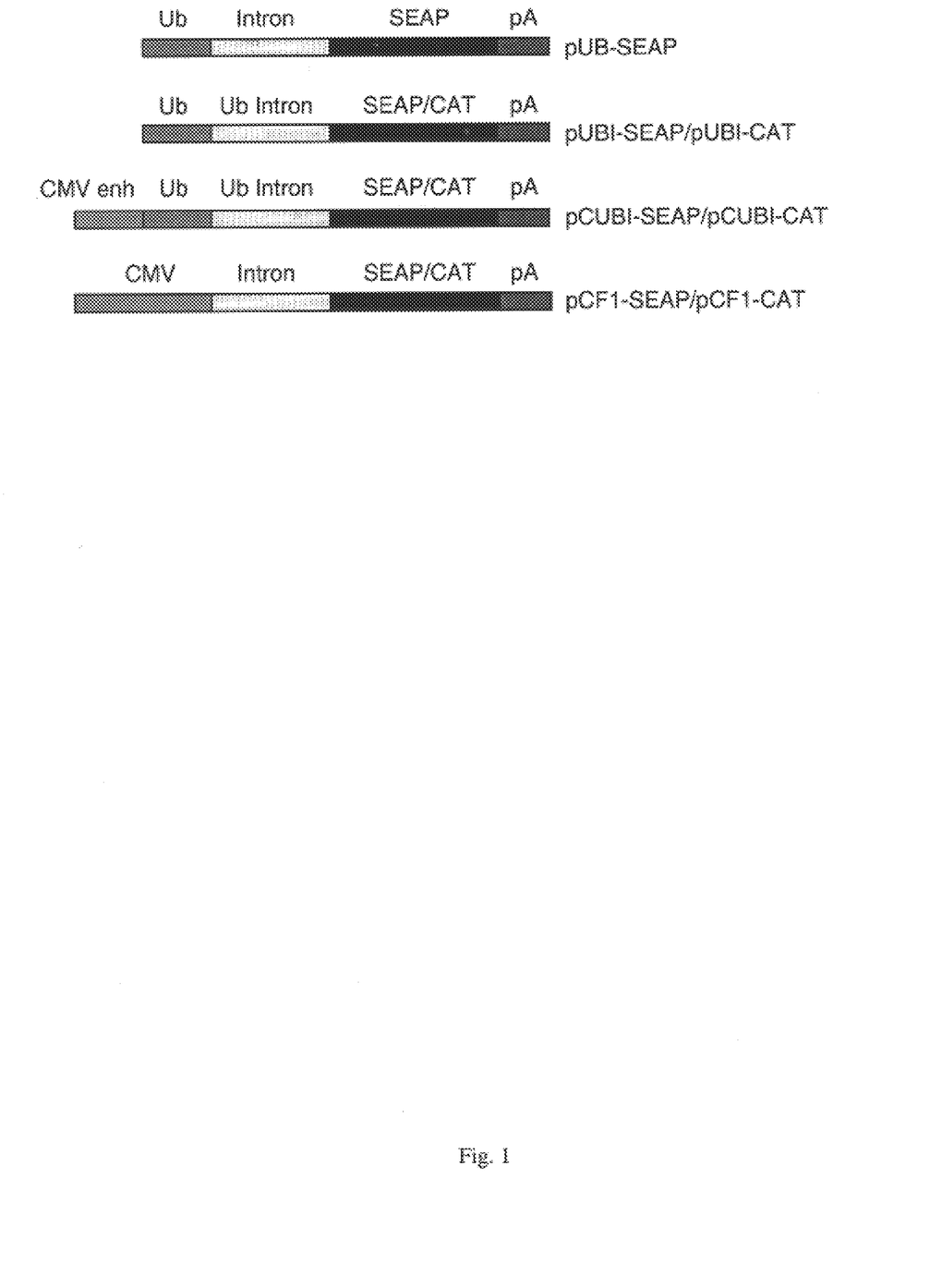

Transgene Expression from the Ubiquitin Promoter in Cultured Human Airway Epithelial Cells The pDNA vectors used in these studies are shown in FIG. 1. The pUB-SEAP plasmid contains the secreted form of the human placental alkaline phosphatase (SEAP) cDNA under the transcriptional control of the human ubiquitin B (Ub) promoter, and contains an intron (a hybrid of an adenoviral and mouse immunoglobulin gene intron) immediately downstream of the Ub promoter sequence. The plasmid pUBI-SEAP is identical to pUB-SEAP except that it contains the ubiquitin B intron in place of the hybrid intron. The control plasmid pCF1-SEAP contains the human cytomegalovirus (CMV) immediate early gene enhancer and promoter sequence.

Figure 2:
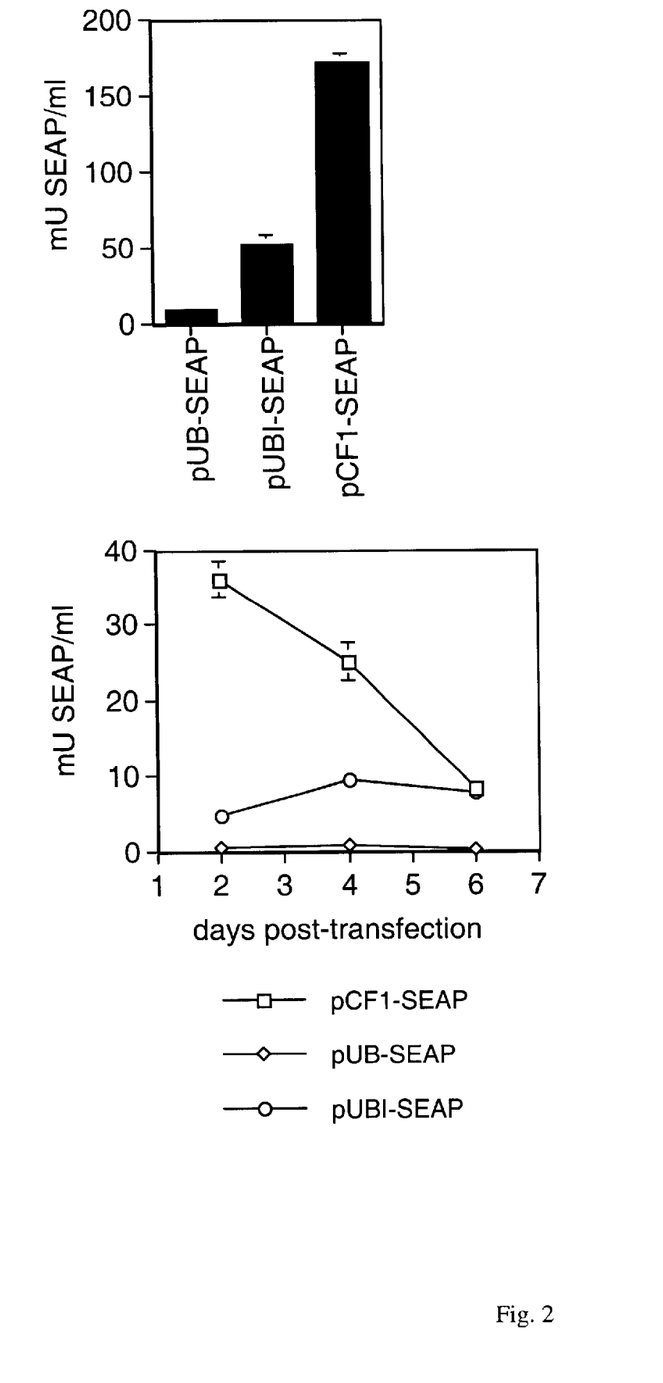
FIG. 2. SEAP expression from pUB-SEAP and pUBI-SEAP in human airway epithelial cells. A) CFT-1 cells were transfected with either pUB-SEAP, pUBI-SEAP, or pCF1-SEAP complexed with cationic lipid GL-67 (10.5 µM GL-67:30 µM pDNA). The tissue culture media was collected 2 days after transfection and assayed for SEAP expression. B) BEAS cells were transfected either with pUB-SEAP, pUBI-SEAP, or pCF1-SEAP complexed with cationic lipid GL-67 (10.5 µM GL-67:30 µM pDNA). The tissue culture media was collected 2, 4, and 6 days after transfection and assayed for SEAP expression. n=4 wells per pDNA. Data are expressed as mean±SEM.

We initially measured expression from the Ub promoter in lung epithelial cells because of our interest in non-viral mediated gene delivery for pulmonary indications. CFT1 cells, a CF human airway epithelial cell line, were transfected with either pUB-SEAP, pUBI-SEAP, or pCF1-SEAP and the levels of SEAP in the media were assayed two days later (FIG. 2A). Expression from pUB-SEAP was much lower than from pCF1-SEAP containing the CMV promoter. Expression from pUBI-SEAP was also lower than pCF1-SEAP, but approximately 5 fold higher compared to pUB-SEAP, demonstrating a beneficial effect on expression using the ubiquitin gene's own intron. The constructs were also transfected into BEAS cells, a human bronchial epithelial cell line, and SEAP expression was measured for six days (FIG. 2B). As was observed in CFT1 cells, SEAP expression from pCF1-SEAP was significantly higher than from pUB-SEAP or pUBI-SEAP at day 2 post-transfection. However, by day 6 post-transfection, expression from pCF1-SEAP had fallen markedly, while expression from pUBI-SEAP was more constant. The cell number and confluence of each well were equivalent, with no evidence of increased toxicity in cells that were transfected with pCF1-SEAP compared to cells that received pUBI-SEAP. These in vitro data suggested that pDNA vectors harboring the ubiquitin promoter provided lower but more stable transgene expression compared to vectors containing the CMV promoter.

Persistence of Transgene Expression from pUBI-CAT in the Mouse Lung

Figure 3:
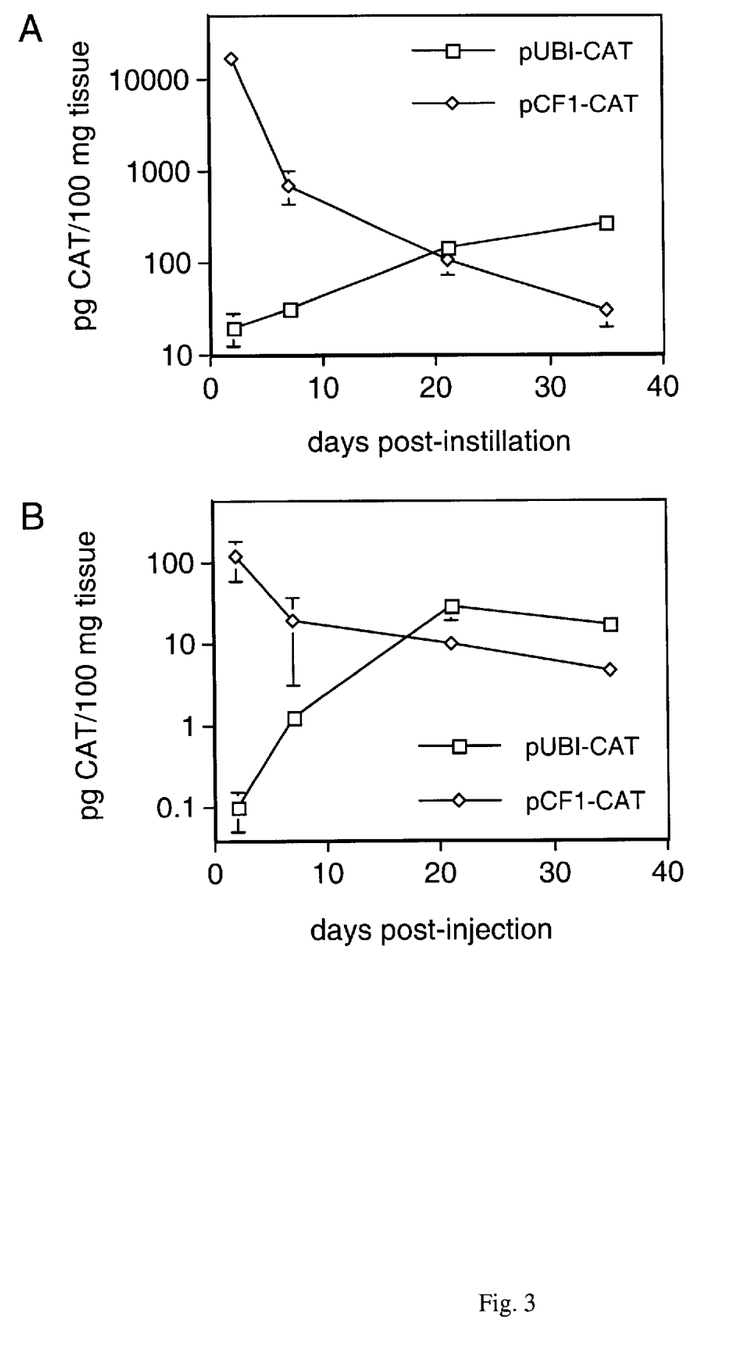

To examine whether the above observed profile of expression was also realized in vivo, we measured the level and duration of CAT expression from pUBI-CAT in the mouse lung. The expression profile was compared to the plasmid pCF1-CAT, which contains the CMV promoter. The pDNAs were complexed with cationic lipid GL-67 and then instilled intranasally into nude BALB/c mice. Immunodeficient mice were used to avoid the complications of an immune response to the *Escherichia coli* CAT enzyme in assessing promoter persistence. Consistent with previously observed results [24], expression from pCF1-CAT was initially high at day 2 after instillation, but then decreased 100 fold within the first 21 days (FIG. 3A). In contrast, expression from pUBI-CAT was very low at day 2, but then increased steadily over time, and by day 35 was approximately 8–10 fold higher than the levels of CAT from pCF1-CAT at this timepoint. When the pUBI-CAT vector was administered intravenously, CAT expression was again initially extremely low, almost at undetectable levels at day 1 after injection (FIG. 3B).

However, by day 35 expression had increased by two logs and was 3- to 4-fold higher than the levels of CAT from pCF1-CAT at this time point. Hence greater persistence of transgene expression was attained in both lung epithelial and endothelial cells in vivo when the transgene was under the transcriptional control of the ubiquitin promoter.

Persistence of Transgene Expression from pCUBI-CAT in the Mouse Lung

Although significantly prolonged, the levels of transgene expression from pUBI-CAT are likely too low to be of practical use. To increase the absolute levels of transgene expression, we appended a portion of the human CMV enhancer immediately 5' to the ubiquitin B promoter sequence to create pCUBI-CAT (FIG. 1). For the in vivo studies, cationic lipid-pCUBI-CAT complexes were instilled into nude BALB/c mice and the levels of CAT expression in the lung were measured for up to 84 days (FIG. 4A). Although lower compared to pCF1-CAT, initial CAT expression from pCUBI-CAT was significantly increased (approximately 2 logs) compared to pUBI-CAT which lacks the CMV enhancer (cf. FIG. 3). As seen previously, CAT expression from pCF1-CAT declined rapidly within the first few weeks, with negligible CAT expression remaining at day 84. In contrast, CAT expression from pCUBI-CAT was nearly constant over this time period, retaining approximately 50% of day 2 CAT levels at day 84. Groups of mice were also given a second dose of pCUBI-CAT to determine if redosing could further augment the levels of expression (FIG. 4B). CAT expression at day 28 from mice that received a second dose on day 26 increased approximately two fold over those mice that received a single dose, and this difference persisted to day 84. The levels of CAT from the redosed mice at day 84 were approximately 100% of day 2 levels. These results indicated that the CMV-Ub hybrid promoter could provide robust, essentially undiminished expression for at least 12 weeks, and that redosing could provide incrementally higher levels of sustained expression.

Sustained Transgene Expression from pCUBI-SEAP in the Mouse Liver

Figure 5:
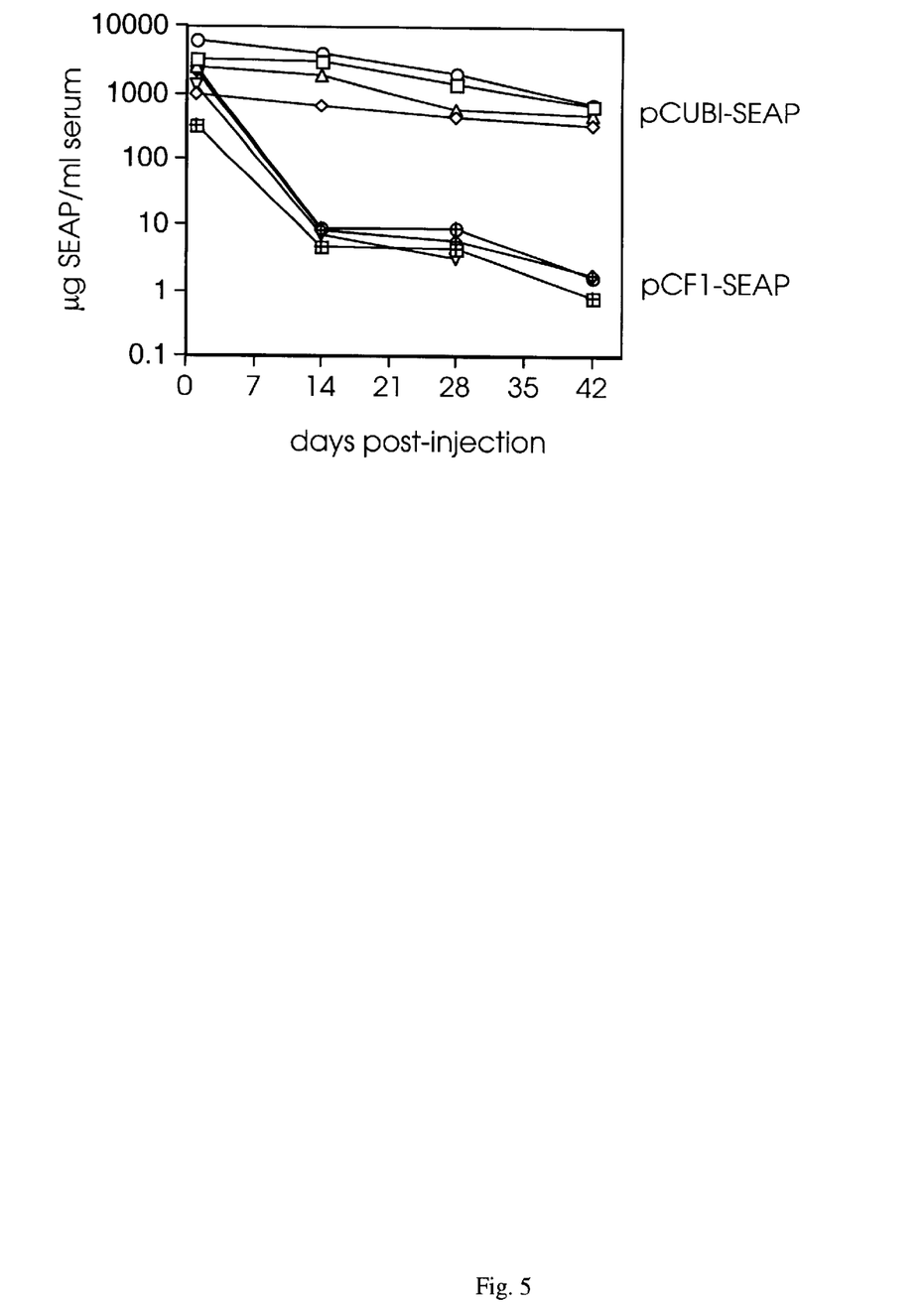
FIG. 5. Persistence of SEAP expression from pCUBI-SEAP in the mouse liver. 1.9 ml of Mirus delivery solution (see Methods) containing 10 µg of pCUBI-SEAP or pCF1-SEAP was injected via the tail vein into Beige/SCID mice. Blood was collected at 1, 14, 28, and 42 days post-injection and the levels of SEAP activity in the serum was measured. Each line represents an individual mouse.

The liver is another major target organ for both viral and synthetic gene delivery vectors. To determine the expression profile of the CMV-ubiquitin hybrid promoter in the liver, pDNA was delivered using a protocol that efficiently transduces liver hepatocytes (see Methods). 10 ug of pCUBI-SEAP or pCF1-SEAP was injected via the tail vein into beige/SCID mice and the levels of SEAP secreted in the serum were measured at days 1, 14, 28, and 42 days after injection (FIG. 5). The initial levels of SEAP in the serum were extremely high (greater than 1 mg/ml at day 1) from both pCUBI-SEAP and pCF1-SEAP. As was seen in the lung, expression from pCF1-SEAP declined sharply within the first two weeks, with low levels at day 42. Expression from pCUBI-SEAP declined much more slowly, with significant levels of SEAP remaining at day 42. The levels of SEAP in the liver were also correspondingly high (1198 ug SEAP±208 ug per 100 mg tissue) at day 42. These results indicated that the CMV-Ub hybrid promoter could also provide sustained expression from the liver as well as the lung.

Figure 6:
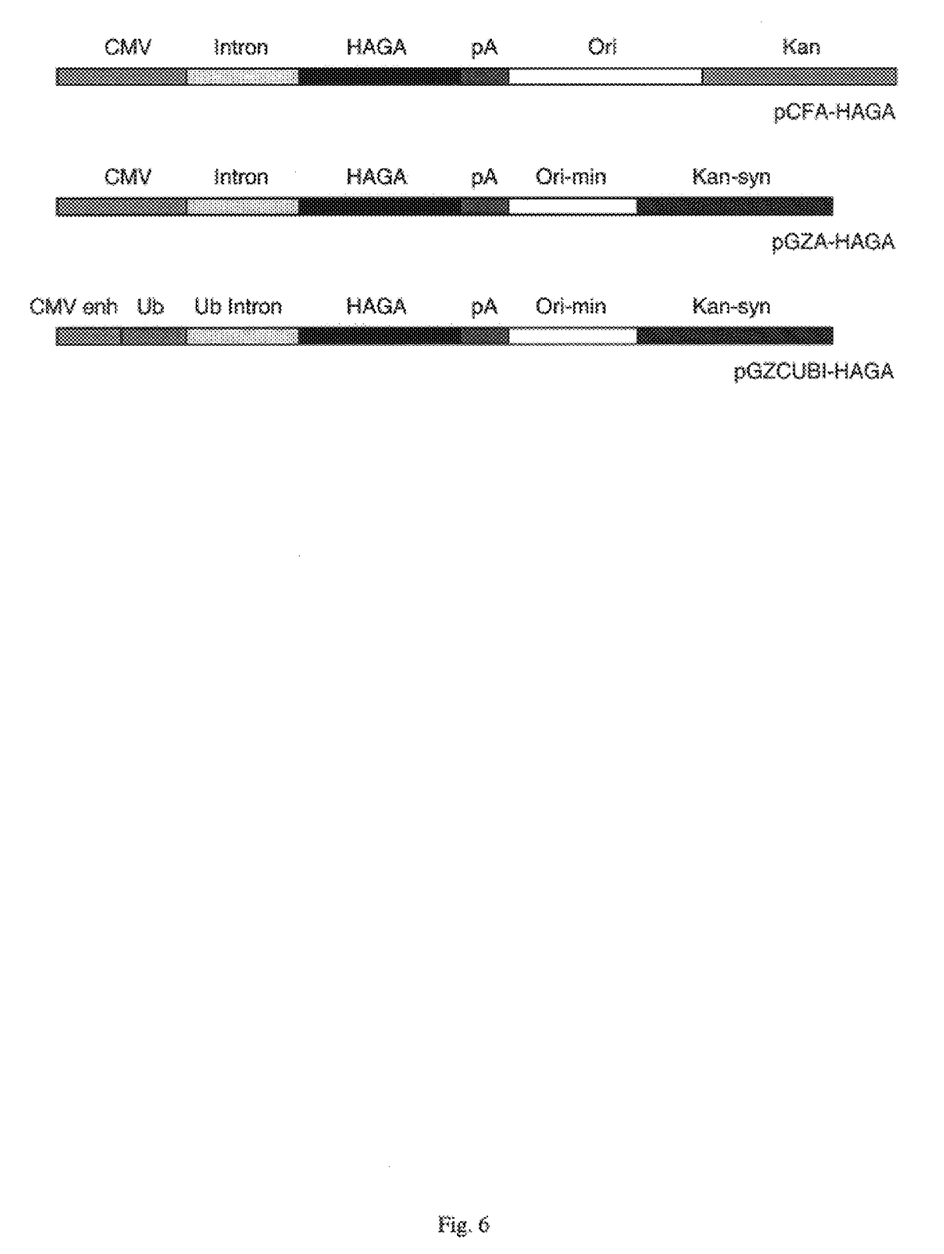
Figure 7:
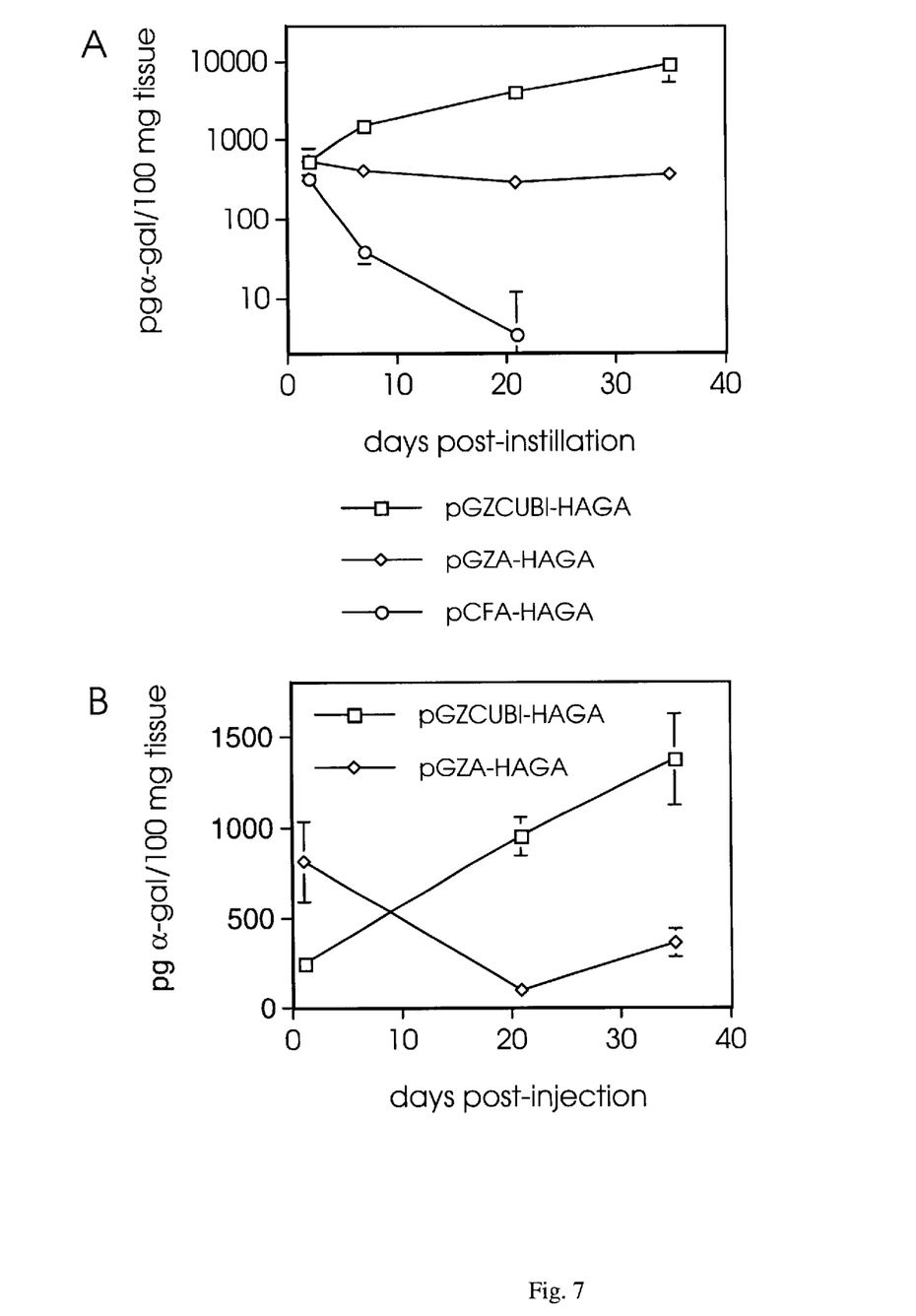
FIG. 7. Persistence of α-galactosidase A expression from pGZCUBI-HAGA and pGZA-HAGA in the mouse lung. A) 75 µl of cationic lipid GL-67 complexed with either pGZCUBI-HAGA, pGZA-HAGA or pCFA-HAGA (0.6:3.6 mM GL-62:pDNA) was instilled intranasally into nude BALB/c mice. B) 100 µl of cationic lipid GL-62 complexed with either pGZCUBI-HAGA or pGZA-HAGA (0.6:3.6 mM GL-62:pDNA) was injected intravenously into nude BALB/c mice. For both A) and B), lungs were harvested at different days post-administration and the levels of α-galactosidase A were measured by an ELISA. n=4 mice per group. Data are expressed as mean±SEM.

Persistence of Transgene Expression from a CpG-Reduced CMV-Ubiquitin Promoter Vector We and others have shown previously that the immunostimulatory CpG motifs present in the pDNA vector play a major role in eliciting an acute inflammatory response after IN or IV delivery of cationic lipid-pDNA complexes [25, 26]. To make the pCUBI vector more suitable for systemic use, we constructed a CpG-reduced version, pGZCUBI, which contains an unmodified Ub promoter and intron but a CpG-reduced backbone composed of a synthetic, non-CpG gene conferring resistance to kanamycin and a minimal replication origin. Into this vector we inserted the cDNA encoding human alpha-galactosidase A (HAGA)(FIG. 6). The pGZCUBI-HAGA vector contains 306 CpG motifs (counting both strands of the pDNA), comparable to pGZA-HAGA, a CpG-reduced vector expressing alpha-galactosidase A from the CMV promoter that contains 292 CpG motifs. In contrast, the non-CpG reduced CMV promoter vector pCFA-HAGA contains 482 CpG motifs. Complexes containing either pGZCUBI-HAGA, pGZA-HAGA, or pCFA-HAGA were instilled IN or injected IV into nude BALB/c mice and the levels of alpha-galactosidase A expression in the lung were measured over time (FIG. 7). After IN delivery, alpha-galactosidase A expression from pCFA-HAGA declined rapidly, as was observed previously with CAT expression from pCF1-CAT (FIG. 7A). However, expression from the CpG-reduced pGZA-HAGA was significantly more persistent, with undiminished levels out to day 35. Expression of alpha-galactosidase A from pGZCUBI-HAGA was comparable to both pCFA-HAGA and pGZA-HAGA at day 2 post-instillation, but then rose steadily over time and at day 35 expression was ten fold higher than the initial levels at day 2 (FIG. 7A).

Figure 4:
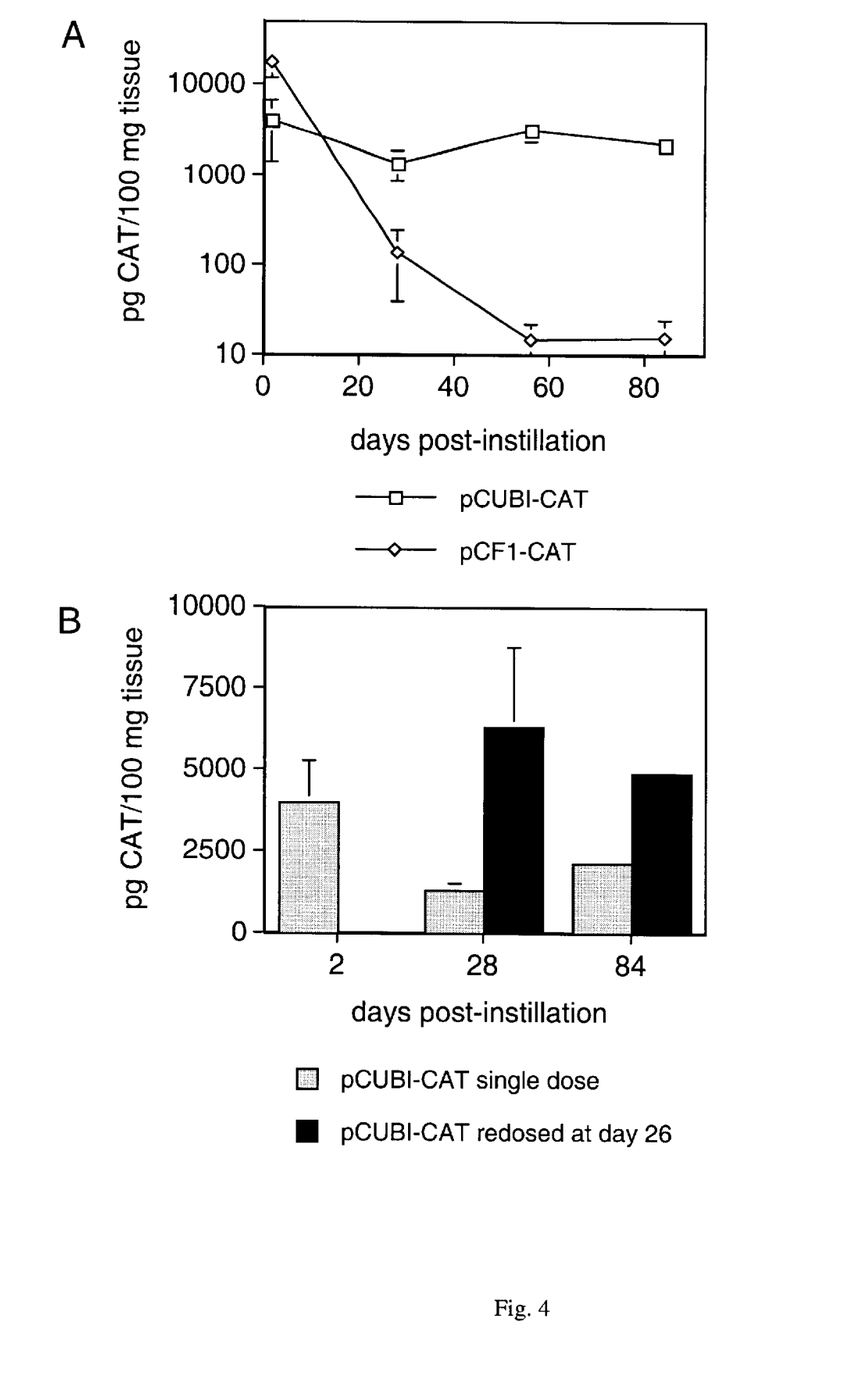

After IV delivery, alpha-galactosidase A expression from pGZA-HAGA declined through day 21, and then recovered slightly at day 35 (FIG. 7B). Expression from pGZCUBI-HAGA, while initially lower than that of pGZA-HAGA, increased steadily through the 35 day time period. Taken together, these results indicated that the CMV-Ub promoter conferred sustained expression of alpha-galactosidase, and that reducing the CpG content of the pDNA alone also improved the persistence of alpha-galactosidase expression. CpG reduction was not required for sustained expression from the CMV-Ub promoter, as was demonstrated with the non-CpG reduced vectors pCUBI-CAT and pCUBI-SEAP (FIGS. 4 and 5). But when both CpG reduction and the CMV-Ub promoter were incorporated into a vector, the levels of alpha-galactosidase A at day 35 from both IN and IV delivery were not only sustained, but significantly higher than starting levels.

Materials and Methods

Plasmid Vector Constructions

To construct pUB-SEAP, which expresses the secreted form of human placental alkaline phosphatase (SEAP), the human ubiquitin B promoter [17] was amplified from human genomic DNA (Clontech Laboratories Inc., Palo Alto, Calif.) using the polymerase chain reaction (PCR) with Pfu polymerase. The amplified sequence corresponds to nucleotides −1093 to −741 relative to the A residue of the ATG initiation codon. The CMV promoter in pCF1-SEAP [8] was excised with PmeI and XbaI and replaced with the PCR product containing the UBB promoter to form pUB-SEAP. To construct pUBI-SEAP, the human UBB promoter and intron were amplified by PCR as above, then inserted into pBC12/PL/SEAP (Tropix, Bedford, Mass.) positioning the translation initiating ATG of SEAP in place of the ubiquitin ATG codon. The UBB promoter-intron-SEAP fragment was excised with BglII and XhoI, blunted with the Klenow fragment of DNA polymerase I, then inserted into the blunted PmeI and NotI sites of pCFA [8] to create pUBI-SEAP. pUBI-CAT was constructed in a similar fashion as pUBI-SEAP, inserting the UBB promoter and intron upstream of CAT.

Figure 8:
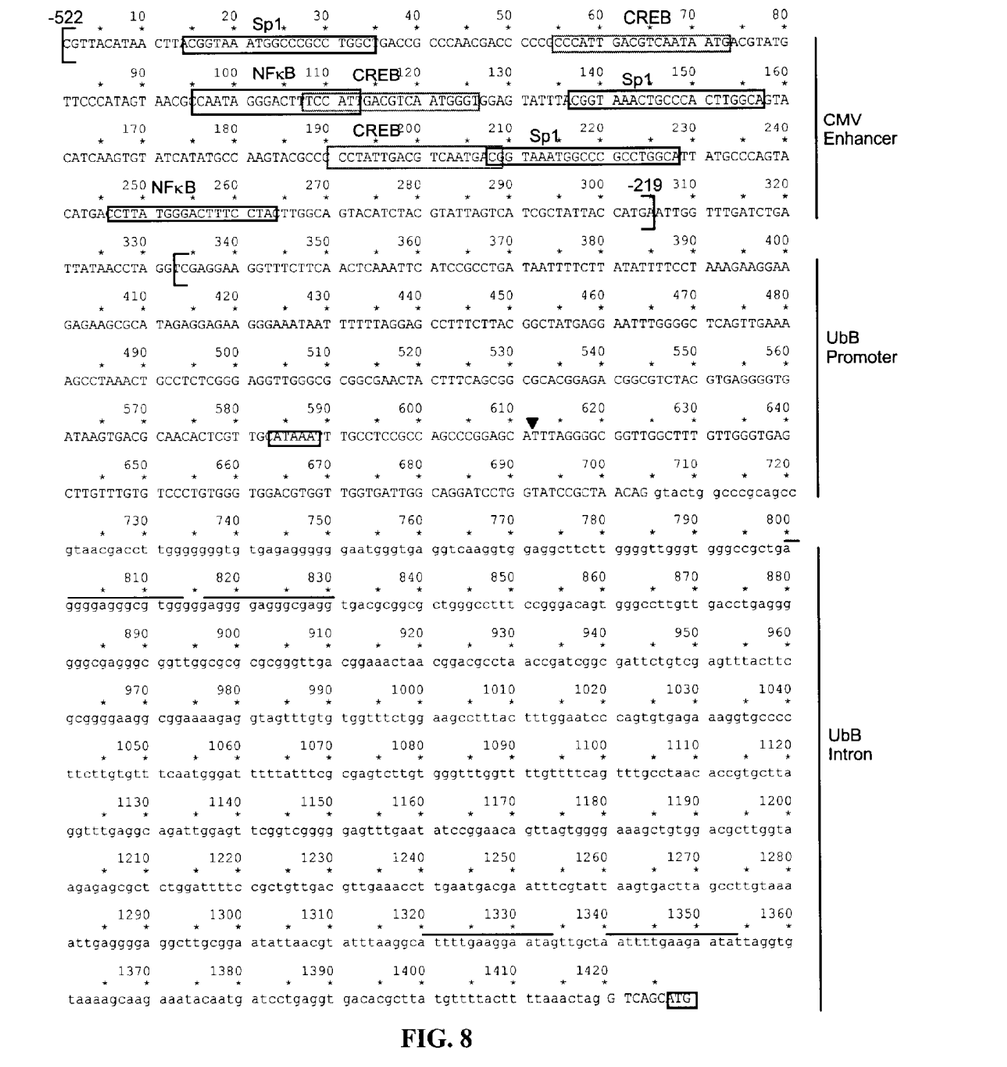

To construct pCUBI-SEAP, pUBI-SEAP was linearized with MfeI and blunted. pCFA was digested with SphI and NcoI, blunted, and the 300 bp CMV enhancer fragment was purified. The CMV enhancer fragment was ligated into the MfeI site of pUBI-SEAP to form pCUBI-SEAP. The sequence of the enhaner/promoter/intron region of pCUBI-SEAP/pCUBI-CAT is shown in FIG. 8. To construct pCUBI-CAT, pCUBI-SEAP was digested with BamHI and SphI, and the 3.2 kb vector backbone fragment was isolated. pUBI-CAT was digested with BamHI and SphI, the 1.7 kb fragment containing the UBB intron-CAT cDNA-BGH poly A was isolated and then ligated to the 3.2 kb fragment to form pCUBI-CAT.

To construct pCFA-HAGA, which expresses human alpha-galactosidase A (HAGA), pCFA was digested with NotI and then blunted with the Klenow fragment of DNA polymerase I. The human alpha-galactosidase A cDNA was excised from pGB83 (kindly provided by Dr. G. Barsomian) with BamHI and EcoRI, blunted with Klenow, and ligated into the blunted NotI site of pCFA to from pCFA-HAGA. To construct the CpG reduced vector pGZA-HAGA, pGZA-sCAT (previously named pGZA-CAT)[35] was digested with NotI (to remove the sCAT cDNA), blunted, and the vector backbone was purified. This vector backbone contains a synthetic non-CpG kanamycin resistance gene and a minimal replication origin region [35]. The blunted human alpha-galactosidase A cDNA fragment from pGB83 (see above) was then ligated into the blunted NotI site of pGZA to form pGZA-HAGA.

To construct the CpG reduced vector pGZCUBI-HAGA, the CMV enhancer-UBB promoter-UBB intron region was amplified by PCR from pCUBI-CAT using PCR primers that incorporate an MfeI site at the 5' end and a NotI site at the 3' end of the PCR product. The PCR product was cloned into a shuttle vector, then excised with MfeI and NotI. pGZA-sCAT was digested with MfeI and NotI, removing the CMV promoter-intron-sCAT cDNA, and the PCR product was ligated in to create pGZCUBI. The blunted human alpha-galactosidase A cDNA fragment from pGB83 (see above) was then ligated into the blunted NotI site of pGZCUBI to create pGZCUBI-HAGA.

Cationic Lipids and Plasmid DNA

The cationic lipids GL-67 (N4-spermine cholesterylcarbamate) and GL-62 (N$^1$-spermine cholesterylcarbamate) have been described previously [24]. Dioleoylphosphatidylethanolamine (DOPE), diphytanoylphosphatidylethanolamine (DphPE), and dimyristoylphosphatidylethanolamine (DMPE) covalently coupled to polyethylene glycol having an average molecular weight of 5000 Daltons (DMPE-PEG$_{5000}$) were purchased from Avanti Polar Lipids, Inc. (Alabaster, Ala.). GL-67 was formulated as GL-67:DOPE:DMPE-PEG$_{5000}$ (1:2:0.05 mol:mol) and GL-62 was formulated as GL-62:DPhPE:DMPE-PEG$_{5000}$ (1:1:0.05 mol:mol) as described [24].

Plasmid DNA was purified by alkaline lysis, ultrafiltration and column chromatography [24]. The purified pDNA used in these studies contained less than 10 ug E. coli chromosomal DNA per mg pDNA and less than 10 endotoxin units per mg pDNA as determined by the chromogenic Limulus amebocyte lysate assay (BioWhittaker, Walkersville, Md.).

In Vitro Transfections

CFT 1 cells, an immortalized human tracheal epithelial cell line from a cystic fibrosis (CF) patient, were kindly provided by Dr. James Yankaskas [37]. BEAS cells, a human bronchial epithelial cell line, were obtained from the American Type Culture Collection (Manassas, Va.). Cells were seeded onto 24 well tissue culture plates at a density of $2\times10^5$ cells per well. 0.5 ml of cationic lipid GL-67:pDNA (10.5:30 uM) complexes was added to each well. Five hours after transfection the complexes were removed and replaced with fresh media. The levels of SEAP in the cell culture media were measured forty-eight hours later. Four wells were transfected for each pDNA vector.

Administration of Cationic Lipid:pDNA Complexes and Naked pDNA into Mice

For intrapulmonary delivery, BALB/c (nu/nu) mice were instilled intranasally with 75 ul of cationic lipid GL-67:pDNA (0.6:3.6 mM) as described previously [24]. For systemic delivery, mice were injected via the tail vein with 100 ul of cationic lipid GL-62:pDNA (0.75:0.75 mM or 1:1 mM). For delivery of pDNA to the liver, mice were injected (Mirus Corporation, Madison, Wis.) via the tail vein using the rapid, high volume protocol described by Zhang et al. [38]. Briefly, 10 ug of plasmid DNA (at 1 mg/ml) was mixed with a 1:1 (v:w) ratio of Trans IT In Vivo Polymer solution (Mirus Corporation), adjusted to a volume of 200 ul with water, vortexed for 2–4 sec, and then incubated at room temperature for 5 min. The solution was then diluted to approximately 2 ml in the Mirus Delivery Solution, and then injected into the tail vein over a period of 6–8 sec. Using this procedure, the pDNA has been shown to be taken up primarily by the liver hepatocytes [38,39]. At 14, 28 and 42 days after injection, mice were anaesthetized and blood was collected by retro-orbital bleeding. The serum was then stored at −80° C.

Enzyme Assays

The levels of SEAP secreted into the media of tissue culture cells were measured using a fluorescent enzyme activity assay as described [8]. The levels of SEAP in mouse serum were assayed using a calorimetric assay. Serum was diluted up to 1:200 in phosphate-buffered saline, and then heat inactivated at 65° C. for 20 min. Alkaline phosphatase reagent (150 ul)(Sigma Diagnostics, St. Louis, Mo.) was added to 50 ul of diluted sample (in a 96 well plate), incubated at room temperature for 10 min, and then the absorbance at 405 nm was measured. Human placental alkaline phosphatase (Calbiochem, San Diego, Calif.) was used as a standard. CAT enzyme activity was measured from lung homogenates as described [24]. Levels of alphagalactosidase A in the lung were quantitated by an enzyme-linked immunosorbent assay (ELISA) using a polyclonal antibody to alpha-galactosidase A as described [23]. This antibody specifically recognizes human and not mouse alpha-galactosidase A.

The above examples are non-limiting, and are included for illustrative purposes only. The skilled artisan, having read the disclosure contained herein, will readily appreciate that many modifications, additions and improvements are possible. Such modifications, additions and improvements are part of the present invention. The disclosure of each and every publication mentioned in this specification is hereby incorporated by reference for the teachings contained therein.

I claim:

1. A recombinant expression vector comprising one or more enhancers linked to the 5' end of a ubiquitin promoter operably linked to a DNA sequence encoding a therapeutic gene.

2. The recombinant expression vector of claim 1, wherein the ubiquitin promoter is isolated from a gene selected from the group consisting of human ubiquitin A, ubiquitin B and ubiquitin C.

3. The recombinant expression vector of claim 2, wherein the enhancer is selected from the group consisting of a cytomegalovirus (CMV) enhancer, an elongation factor 1-alpha enhancer; endothelial enhancers and liver-specific enhancers.

4. The recombinant expression vector of claim 3, wherein the enhancer is a CMV enhancer.

5. The recombinant expression vector of claim 4, wherein the expression vector has been altered to eliminate at least one CpG sequence present in the native sequences.

6. The recombinant expression vector of claim 4, wherein the ubiquitin promoter is isolated from human ubiquitin B.

7. The recombinant expression vector of claim 4, wherein the therapeutic gene is selected from the group consisting of factor VIIa, factor VIII, and factor IX.

8. The recombinant expression vector of claim 4, wherein the therapeutic gene is selected from the group consisting of glucocerebrosidase, alpha-galactosidase, acid alpha-glucosidase, alpha-n-acetylgalactosaminidase, acid sphingomyelinase and alpha-iduronidase.

9. The recombinant expression vector of claim 4, wherein the therapeutic gene is selected from the group consisting of CFTR, dystrophin and alpha-1-antitrypsin.

10. A recombinant expression vector comprising a CMV enhancer linked to the 5' end of a promoter isolated from human ubiquitin B operably linked to a DNA sequence encoding alpha-galactosidase.

11. A recombinant expression vector comprising a CMV enhancer linked to the 5' end of a promoter isolated from human ubiquitin B operably linked to a DNA sequence encoding glucocerebrosidase.

* * * * *

SEQUENCE LISTING

<160> NUMBER OF SEQ ID NOS: 1

<210> SEQ ID NO 1
<211> LENGTH: 1428
<212> TYPE: DNA
<213> ORGANISM: CMV enhancer-ubiquitin B promoter and introgen region

<400> SEQUENCE: 1

```
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catgaattgg tttgatctga ttataaccta ggtcgaggaa ggtttcttca actcaaattc     360
atccgcctga taattttctt atattttcct aaagaaggaa gagaagcgca tagaggagaa     420
gggaaataat tttttaggag cctttcttac ggctatgagg aatttggggc tcagttgaaa     480
agcctaaact gcctctcggg aggttgggcg cggcgaacta ctttcagcgg cgcacggaga     540
cggcgtctac gtgagggtg ataagtgacg caacactcgt tgcataaatt tgcctccgcc      600
agcccggagc atttagggc ggttggcttt gttgggtgag cttgtttgtg tccctgtggg      660
tggacgtggt tggtgattgg caggatcctg gtatccgcta acaggtactg gcccgcagcc     720
gtaacgacct tggggggtg tgagagggg gaatgggtga ggtcaaggtg gaggcttctt       780
ggggttgggt gggccgctga ggggagggcg tgggggaggg gagggcgagg tgacgcggcg     840
ctgggccttt ccgggacagt gggccttgtt gacctgaggg gggcgagggc ggttggcgcg     900
cgcgggttga cggaaactaa cggacgccta accgatcggc gattctgtcg agtttacttc     960
gcggggaagg cggaaaagag gtagtttgtg tggtttctgg aagcctttac tttggaatcc    1020
cagtgtgaga aggtgcccc ttcttgtgtt tcaatgggat ttttatttcg cgagtcttgt     1080
gggtttggtt ttgttttcag tttgcctaac accgtgctta ggtttgaggc agattggagt    1140
tcggtcgggg gagtttgaat atccggaaca gttagtgggg aaagctgtgg acgcttggta    1200
agagagcgct ctggattttc cgctgttgac gttgaaacct tgaatgacga atttcgtatt    1260
aagtgactta gccttgtaaa attgagggga ggcttgcgga atattaacgt atttaaggca    1320
ttttgaagga atagttgcta attttgaaga atattaggtg taaaagcaag aaatacaatg    1380
atcctgaggt gacacgctta tgttttactt ttaaactagg tcagcatg                 1428
```